(12) United States Patent
Dentinger (10) Patent No.: US 9,204,857 B2
(45) Date of Patent: Dec. 8, 2015

(54) SYSTEM AND METHOD FOR MONITORING HEMODYNAMIC STATE

(75) Inventor: Aaron Mark Dentinger, Latham, NY (US)

(73) Assignee: General Electric Company, Niskayuna, NY (US)

( * ) Notice: Subject to any disclaimer, the term of this patent is extended or adjusted under 35 U.S.C. 154(b) by 987 days.

(21) Appl. No.: 12/478,831

(22) Filed: Jun. 5, 2009

(65) Prior Publication Data
US 2010/0312115 A1    Dec. 9, 2010

(51) Int. Cl.
| | |
|---|---|
| A61B 8/00 | (2006.01) |
| A61B 8/04 | (2006.01) |
| A61B 5/021 | (2006.01) |
| A61B 5/024 | (2006.01) |
| A61B 5/08 | (2006.01) |
| A61B 5/145 | (2006.01) |

(52) U.S. Cl.
CPC .............. *A61B 8/04* (2013.01); *A61B 5/02116* (2013.01); *A61B 5/024* (2013.01); *A61B 5/0816* (2013.01); *A61B 5/145* (2013.01)

(58) Field of Classification Search
CPC .... A61B 5/02116; A61B 5/024; A61B 5/145; A61B 5/0816; A61B 8/04
USPC ........................................................ 600/450
See application file for complete search history.

(56) References Cited

U.S. PATENT DOCUMENTS

| | | | |
|---|---|---|---|
| 4,519,395 A * | 5/1985 | Hrushesky | 600/484 |
| 5,188,106 A | 2/1993 | Nappholz et al. | |
| 5,295,486 A * | 3/1994 | Wollschlager et al. | 600/447 |
| 5,713,367 A * | 2/1998 | Arnold et al. | 600/517 |
| 6,176,832 B1 * | 1/2001 | Habu et al. | 600/485 |
| 7,048,691 B2 | 5/2006 | Miele et al. | |
| 2002/0055672 A1 | 5/2002 | Zhang | |
| 2002/0055680 A1 | 5/2002 | Miele et al. | |
| 2002/0099298 A1 * | 7/2002 | Yokozeki | 600/494 |
| 2003/0158493 A1 * | 8/2003 | Goor et al. | 600/513 |
| 2004/0236187 A1 * | 11/2004 | Bock et al. | 600/300 |

(Continued)

OTHER PUBLICATIONS

Drzewiecki et al., Vessel growth and collapsible pressure-area relationship, 1997, Am J Physiol Heart Circ Physiol 273:H2030-H2043.*

(Continued)

*Primary Examiner* — Bo J Peng
(74) *Attorney, Agent, or Firm* — Melissa K. Dobson (57) ABSTRACT

A method for continuous non-invasive hemodynamic state monitoring in a subject. The method includes acquiring continuous ultrasound data, estimating continuous arterial waveforms based upon the acquired ultrasound data, and deriving hemodynamic parameters for each cardiac cycle from the arterial waveforms. The method further includes defining a current hemodynamic state of the subject by setting limits on one or more hemodynamic parameters based upon the variation of these parameters over an initial period of time, and continuously monitoring a hemodynamic state of the subject. Further, a current state for one or more hemodynamic parameters of the subject are compared to previously determined limits for the one or more hemodynamic parameters, and either an alarm is triggered in an event that a change is detected in the current state of the one or more hemodynamic parameters or the arterial parameters are converted into a continuous estimate of the arterial blood pressure.

7 Claims, 7 Drawing Sheets

(56) References Cited

U.S. PATENT DOCUMENTS

2005/0033174 A1    2/2005  Moehring et al.
2005/0096557 A1*   5/2005  Vosburgh et al. ............. 600/509

OTHER PUBLICATIONS

Lichtenstein et al., Static and Dynamic Mechanical Properties of the Carotid Artery From Normotensive and Hypertensive Rats, 1998, Hypertension, 32:346-350.*

* cited by examiner

SYSTEM AND METHOD FOR MONITORING HEMODYNAMIC STATE

BACKGROUND

The present invention relates generally to methods and apparatus for continuous, non-invasive monitoring of the hemodynamic state and the arterial blood pressure of a subject.

A method for the determination of non-invasive beat-by-beat (continuous) systolic and diastolic arterial blood pressures has long been desired in patient monitoring. Automatic blood pressure cuffs can be used for this application, by inflating them as rapidly as is possible; however, this provides blood pressure data only at 1 to 2 minute intervals, and each inflation can be painful, especially for elderly or hypertensive patients.

A common technique for continuously measuring blood pressure is to insert a saline-filled catheter through the patient's vascular system to the point at which it is desired to perform the measurements. The catheter is connected to a pressure sensor, which measures the pressure in the vessel. An alternative method uses a catheter with a pressure sensor at the tip that directly senses the blood pressure. However, these techniques involve making an incision through the patient's skin and inserting the catheter into a blood vessel. As a consequence, this invasive procedure entails some risk of complications for the patient.

An indirect, non-invasive process for continuously measuring blood pressure is based on the pulse transit time (PTT) which is the difference in time required for a pressure pulse generated from a heart beat to propagate between two points in the vascular system. One apparatus for this technique includes an electrocardiograph that senses electrical signals in the heart to provide an indication when a blood pulse enters the aorta. A pulse oximeter is placed on an index finger of the patient to detect when the blood pressure pulse reaches that location. The pulse transit time between the heart and the index finger is measured and calibrated to the existing blood pressure that is measured by another means, such as by the automated oscillometric method. Thereafter changes in the pulse transit time correspond to changes in the blood pressure. Generally, the faster the transit time the higher the blood pressure. Thus, changes in the pulse transit time can be equated to changes in the blood pressure. However, the electrocardiograph (ECG) senses electrical signals in the heart, which do not indicate the point in time when the blood pressure pulse actually leaves the heart upon the mechanical opening of the aortic valve. A time interval of varying length, known as the cardiac pre-ejection period (PEP), exists between peaks of the QRS wave of the electrocardiogram signal and the aortic valve opening. The inability of prior pulse transit time-based monitors to account for the cardiac pre-injection period results in an inaccurate measurement of the pulse transit time and thus blood pressure. Additionally, changes in the compliance of the blood vessels also affect the pulse transit time estimates. Chronic changes in arterial compliance occur due to aging, arteriosclerosis or hypertension. Arterial compliance can also change acutely due to neural, humoral, myogenic or other influences. Previous monitoring systems have been unable to separate changes due to compliance from changes due to blood pressure. As a consequence, some degree of inaccuracy has existed in calculating blood pressure from the variation of the pulse transit time.

Other indirect, non-invasive techniques for continuously measuring blood pressure are based on biomechanical models to convert continuous indirect arterial measurements into blood pressure readings. These continuous measurement techniques rely on a static biomechanical model derived from either empirical data or a calibration of the model using an independent pressure reading. Similar to PTT, these techniques lack the ability to adapt to acute physiological changes affecting the biomechanical model, such as changes in the arterial compliance.

Two common continuous measures used in these techniques include tonometry and plythesmography. Tonometry measures variations in the pressure at the surface of the skin induced by changes in the arterial pressure. The tonometric sensors are typically placed over small arteries on the hand or wrist, and the measurements are sensitive to motion and alignment. Plythesmography measures changes in the volume of a limb, such as the arm. Since plythesmogrpaphy measures the change in the total volume, contributions from the arterial and venous systems cannot be separated contributing to errors in the arterial blood pressure measurement.

Therefore, an improved blood monitoring system is desirable to address one or more of the aforementioned issues.

BRIEF DESCRIPTION

A method for continuous non-invasive hemodynamic state monitoring in a subject is provided. The method includes acquiring continuous ultrasound data via an ultrasound transducer attached to the subject. The method also includes estimating multiple continuous arterial waveforms based upon the acquired ultrasound data. The method also includes deriving hemodynamic parameters for each cardiac cycle from the arterial waveforms. The method further includes defining a current hemodynamic state of the subject by setting limits on one or more hemodynamic parameters based upon the variation of these hemodynamic parameters over an initial period of time. The method further includes defining an initial biomechanical model of the artery to convert arterial waveforms into a continuous measure of arterial blood pressure. The method also includes continuously monitoring the current hemodynamic state of the subject based upon subsequent ultrasound measurements and the derived hemodynamic parameters from the ultrasound data. The method further includes comparing the current state of the one or more hemodynamic parameters of the subject to the previously determined limits for one or more hemodynamic parameters and performing either of the following: outputting a trigger signal or alarm from the hemodynamic state monitor, redefining the current hemodynamic state of the subject by setting new limits for one or more of the hemodynamic parameters based on recent measurements, and calibrating a new biomechanical model for the current hemodynamic state in an event that a change is detected in the current state of one or more hemodynamic parameters; or converting the waveforms and arterial waveforms in an event that a change in the current state of the one or more hemodynamic parameters is not detected.

In accordance with another embodiment of the invention, a system for continuous non-invasive hemodynamic state monitoring in a subject is provided. The system includes an ultrasound transducer acoustically coupled to the subject configured to acquire multiple ultrasound data. The system also includes an ultrasound processor coupled to the ultrasound transducer. The ultrasound processor is configured to estimate multiple arterial parameters based upon the acquired ultrasound data. The ultrasound processor is also configured to derive hemodynamic parameters for each cardiac cycle from the arterial waveforms. The ultrasound processor is further configured to define a current hemodynamic state of the subject by setting limits on one or more hemodynamic parameters based upon the variation of these parameters over an initial period of time. The ultrasound processor is also configured to define an initial biomechanical model of the artery calibrated for the current hemodynamic state that converts arterial waveforms into a continuous estimate of arterial blood pressure. The ultrasound processor is further configured to continuously monitor a hemodynamic state of the subject based upon the generated generated hemodynamic parameters from subsequent measurements. The ultrasound processor is also configured to compare a current state of the one or more hemodynamic parameters of the subject to previously determined limits of the one or more hemodynamic parameters, and performs either of the following: outputting a trigger signal or alarm from a hemodynamic state monitor, redefining the current hemodynamic state of the subject by setting new limits for one or more of the hemodynamic parameters, based on recent measurements, and calibrate a new biomechanical model for the current hemodynamic state, in an event that a change is detected in the current state of the one or more hemodynamic parameters; or convert the arterial waveforms into a continuous estimate of the arterial blood pressure using the biomechanical model, and outputting the current hemodynamic parameters, blood pressure estimates, and arterial waveforms in an event that a change in the current state of the one or more hemodynamic parameters is not detected. The system also includes a display coupled to the processor configured to output a measured value of the one or more hemodynamic parameters.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As discussed in detail below, embodiments of the invention are directed to a system and method for continuously monitoring hemodynamic state and the arterial blood pressure. A hemodynamic state is defined using arterial waveforms, such as arterial area and volumetric flow rate, and respective hemodynamic parameters generated from the minimum, mean or maximum value of these waveforms over each cardiac or respiratory cycle.

Figure 1:
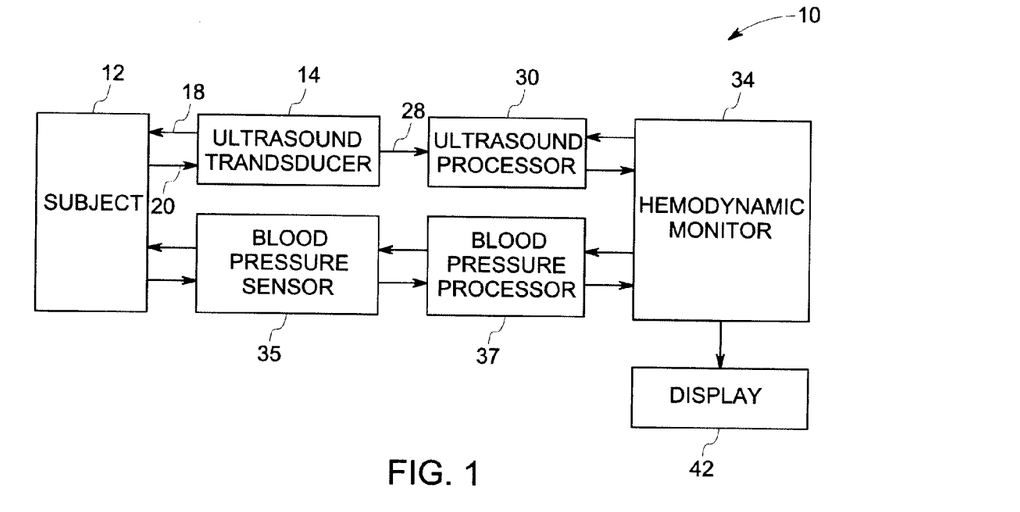
FIG. 1 is a block diagram representation of a system for continuous non-invasive monitoring of the hemodynamic state of a subject in accordance with an embodiment of the invention.

FIG. 1 is a block diagram representation of a system 10 for continuous non-invasive monitoring of hemodynamic state of a subject 12, for example, a living organism. The system 10 includes an ultrasound transducer 14 acoustically coupled to the subject 12 configured to acquire a plurality of ultrasound data. The ultrasound transducer 14 transmits ultrasound signals 18 to the subject 12. Reflected ultrasound signals 20 from the subject 12 are received by the ultrasound transducer 14 and further transmitted as electrical signals 28 to an ultrasound processor 30. The ultrasound processor 30 estimates multiple arterial waveforms based upon the acquired electrical signals 28. In one embodiment, the arterial parameters include continuous waveforms for the arterial area and volumetric flow rate. Details of estimation of the arterial parameters may be obtained in U.S. Pat. No. 7,125,383 and U.S. Pat. No. 7,425,199 entitled "Method and Apparatus for ultrasonic continuous, non-invasive blood pressure monitoring" assigned to the same assignee as this application, the entirety of which is hereby incorporated by reference herein.

The hemodynamic monitor 34 extracts hemodynamic parameters from the arterial waveforms, such as minimum, mean, and maximum value for each cardiac. In addition, the arterial waveforms are use to estimate the heart rate for each cardiac cycle from the period of arterial waveforms. In another embodiment, the heart rate is obtained via an electrocardiograph (ECG) coupled to the subject 12 and the processor 30. Waveforms generated by the ECG are used to estimate heart rate for each cardiac cycle of the subject 12. In another embodiment, the hemodynamic parameters are augmented by measurements such as respiratory rate and oxygenation level measured via ancillary measurement devices. In another embodiment, the hemodynamic parameters are smoothed over a respiratory period using either a manual or automatic measure of the respiratory rate to reduce the variations in the hemodynamic state due to respiration.

Additionally, the hemodynamic monitor 34 continuously monitors the state of the subject based upon the arterial waveforms and generated hemodynamic parameters. The hemodynamic parameters are used to define hemodynamic state on a beat-to-beat basis and to monitor changes in the physiological state. Initial limits for the one or more hemodynamic parameters are determined based upon the measures of the one or more hemodynamic parameters over a period of time. These limits are used to detect a change from the current hemodynamic state recognizing that a change in physiological state of the subject 12 is a possible indication of underlying conditions.

The hemodynamic monitor 34 also generates an initial biomechanical model of the artery, such as a non-linear compliance curve, to translate the multiple arterial waveforms into a continuous measure of the arterial blood pressure in the subject 12. In a particular embodiment, the biomechanical model of the artery includes a static arterial compliance model. In another embodiment, the arterial model includes an adaptable compliance model, as will be discussed in greater detail below. The compliance curve is calibrated using arterial waveforms derived from the ultrasound data and an independent reading of the arterial blood pressure measured with an automated blood pressure device. The automated blood pressure device consists of an inflatable blood pressure cuff or sensor 35 attached to the subject 12 and a separate blood pressure processor 37 for controlling the inflation of the cuff, sensing the oscillations in the back pressure, and estimating the diastolic, mean, and systolic blood pressures.

The current state of the one or more hemodynamic parameters of the subject 12 is compared to the previously determined limits on one or more of the hemodynamic parameters. In an event that a change is detected in the current state of the one or more hemodynamic parameters, a trigger signal or alarm is output from a hemodynamic monitor 34. The hemodynamic monitor 34 initiates the determination of a new set of limits on one or more hemodynamic parameters defining the current hemodynamic parameter and an update to the biomechanical model. In such an event, the curve of the arterial compliance model is recalibrated based upon the current hemodynamic state. In one embodiment, the update to the biomechanical model consists of a recalibration of the static compliance model using the recent ultrasound data and a new blood pressure reading. In another embodiment, the update to the biomechanical model consists of dynamically updating the biomechanical model based on the current hemodynamic state and previously calibrated biomechanical models for observed hemodynamic states. In an event that a change is not detected, the continuous estimates of the arterial blood pressure are estimated using the ultrasound data and biomechanical model. A display 42 coupled to the processor 30 outputs a measured value of the one or more hemodynamic parameters, the arterial waveforms, and estimates of the arterial blood pressure.

It should be noted that embodiments of the invention are not limited to any particular processor for performing the processing tasks of the invention. The term "processor," as that term is used herein, is intended to denote any machine capable of performing the calculations, or computations, necessary to perform the tasks of the invention. The term "processor" is intended to denote any machine that is capable of accepting a structured input and of processing the input in accordance with prescribed rules to produce an output. It should also be noted that the phrase "configured to" as used herein means that the processor is equipped with a combination of hardware and software for performing the tasks of the invention, as will be understood by those skilled in the art.

The hemodynamic parameters derived from arterial area and volumetric flow rate waveforms are used in a biomechanical model to generate continuous estimates of the blood pressure. The approach for blood pressure estimation uses a biomechanical model consisting of an arterial compliance curve to convert continuous area measures into continuous blood pressure estimates.

Figure 2:
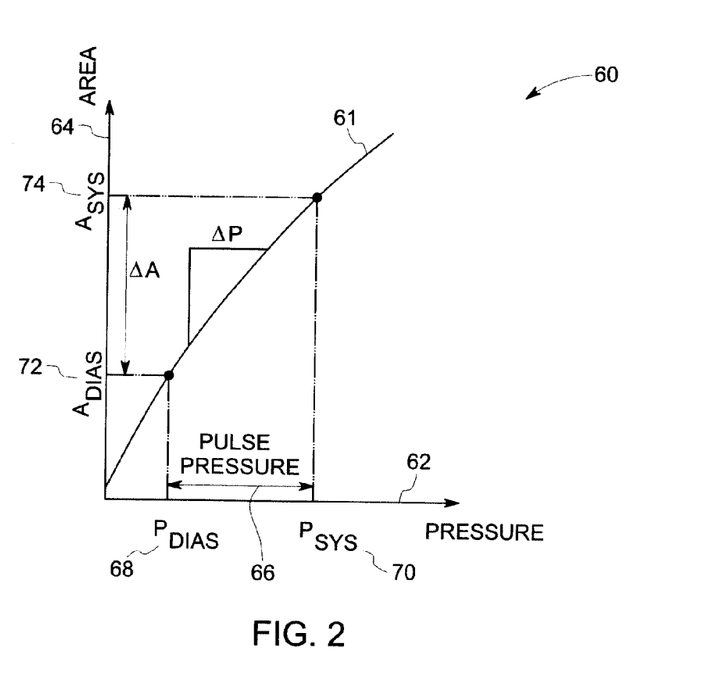
FIG. 2 is a graphical illustration of an exemplary arterial compliance curve employed in a biomechanical model of the artery in accordance with an embodiment of the invention.

FIG. 2 is a graphical illustration 60 of an exemplary compliance curve 61 employed in the arterial compliance model. The compliance curve 61 defines the non-linear relationship between the arterial pressure and arterial area. The X-axis 62 represents pressure, typically measured in units of mmHg, and the Y-axis 64 represents area, typically measured in units of $mm^2$ or $cm^2$. Desired pressures over which an accurate compliance curve is needed may be limited to a range slightly larger than a diastolic-to-systolic range reference by numeral 66. An exponential model of the compliance curve as parameterized in an article by Powalowski T and Pensko B, entitled "A Noninvasive ultrasonic method for the elasticity evaluation of the carotid arteries and its application in the diagnosis of the cerebro-vascular system", Archives of Acoustics, 12, 1-2 pp 109-126, 1988 is sufficient for this application with the pressure given by:

$$p(t) = p_{DIAS} e^{\alpha\left(\frac{A(t)}{A_{DIAS}} - 1\right)} \quad (1)$$

wherein the constant $\alpha$ is:

$$\alpha = \frac{A_{DIAS}}{A_{SYS} - A_{DIAS}} \ln\left(\frac{P_{SYS}}{P_{DIAS}}\right) \quad (2)$$

and $p_{DIAS}$ and $p_{SYS}$ are diastolic and systolic pressures referenced by numerals 68, 70 respectively and $A_{DIAS}$ and $A_{SYS}$ are diastolic and systolic areas referenced by numerals 72, 74 respectively. For a given individual and physiological state, these parameters must be determined to calibrate the biomechanical model. The exponential function has three parameters, $\alpha$, $p_{DIAS}$ and $A_{DIAS}$, that can be calibrated using the diastolic and systolic values for the pressure and area. This requires an independent measure of the diastolic and systolic arterial blood pressures. In the clinical setting, the pressure values are obtained from an automated cuff-based blood pressure reading, while the area values are derived from the continuous ultrasound-based arterial area waveforms in a temporal window just prior to the cuff inflation.

The arterial compliance model includes two types: a static compliance model and an adaptable compliance model. The static compliance model is based on periodic and automatically triggered blood pressure measurements to calibrate a non-linear compliance curve. The calibration of the blood pressure model is accomplished using ultrasound measurements for the minimum, mean, and maximum area taken for a short time period immediately prior to the cuff-based blood pressure reading. Further, the parameter of a non-linear compliance curve will be determined using the equations for the compliance model. Once the compliance model has been calibrated, ultrasound data is used to monitor the hemodynamic parameters and subsequent continuous area measurements from ultrasound are converted to blood pressure estimates. The static compliance model is extended to the dynamic in vivo situation where acute changes in compliance is possible by triggering a new blood pressure reading and recalibration of the compliance curve when the hemodynamic state has changed in order to maintain accuracy of the blood pressure estimation.

The ultrasound data segments used for calibration are also used to define the current hemodynamic state using statistics for the area, flow, and heart rate within the calibration time window. The current hemodynamic parameters will be compared to limits based on initial measurements for area, flow and heart rate to determine if the hemodynamic state has changed. If no change is detected, then the continuous, ultrasound-derived area measurements will be converted to pressure readings using the current compliance model. This processing will continue until the next blood pressure reading at which time the compliance model will be updated. If a change in the hemodynamic state is detected, then a recalibration of the compliance curve will be initiated by triggering another calibration to update the compliance model.

The hemodynamic state is defined by a set of one or more hemodynamic parameters and the variation in the multiple non-invasive measurements used to monitor the hemodynamic state. Using a multivariate normal distribution as an example for the variation in the measurement of the hemodynamic parameters, the hemodynamic state is completely specified by a mean vector and a covariance matrix of the multivariate distribution. For a state defined by n non-invasive hemodynamic parameters, the mean $\mu$ and standard deviation $\Sigma$ are specified by:

$$\mu = E[X] \tag{3}$$

and $$\Sigma = E[(X-\mu)(X-\mu)^T] \tag{4}$$

where X is an [n×1] random vector corresponding to a single measurement of the hemodynamic parameters and E is the expectation of operator. Given a finite set of measurements, the expectations in the above equations (1) and (2) are replaced by sample estimates of the mean and covariance matrix.

The trigger can be set as a threshold on the individual measurement parameters or on a function of these parameters. The threshold can be automatically adjusted based on the statistics of the current hemodynamic state. One example of the trigger uses the mean and standard deviations for the individual parameters in the current hemodynamic state to define upper and lower limits for recalibration. This can be written as $$|x_n - \mu_n| \leq \gamma_n \sigma_n \tag{5}$$

where $\mu_n$ is the mean, $\sigma_n$ is the standard deviation, and $x_n$ is the current measurement for the $n^{th}$ parameter while $\gamma$ determines the threshold for each parameter relative to the standard deviation. This method requires a comparison for each of the n parameters defining the hemodynamic state and a recalibration is trigger when one or more of the parameters exceed the threshold.

A second example of the trigger is to use a threshold on a distance metric to compare the distance in the n-dimensional space between current measurement and the hemodynamic states. One non-limiting example of the distance metric is the Euclidean distance to the mean of measurements defining the different hemodynamic states $$d(X|\mu) = \sqrt{(X-\mu)^T(X-\mu)} \tag{6}$$

where X is the current measurement and $\mu$ is the mean of the current hemodynamic state. The threshold for the trigger is then set based using $$d(X|\mu) \leq d_{threshold} \tag{7}$$

where $d_{threshold}$ is an upper limit on the distance.

A third example of a trigger uses a model of the multivariate probability distribution and sets a threshold on the probability of measurement being in the current hemodynamic state. In comparison to the Euclidean distance metric, this incorporates both the center of the cluster of measurement points and the spread of the measurements around the mean value. Using the multivariate normal distribution example, the probability for hemodynamic state defined by the mean vector $\mu$ and the covariance matrix $\Sigma$ is given by $$P(X|\mu, \Sigma) = \frac{1}{(2\pi)^{n/2}|\Sigma|^{1/2}} e^{-\frac{1}{2}(X-\mu)^T \Sigma^{-1}(X-\mu)} \tag{8}$$

where X is a vector of the current measurement. A single threshold is used to set a lower limit on the probability for triggering the recalibration. The threshold for the trigger based on the probability is $$P(X|\mu, \Sigma) \leq P_{threshold} \tag{9}$$

where $P_{threshold}$ is the probability threshold. The selection of threshold is a tradeoff between the acceptable number of recalibrations and the accuracy of the blood pressure estimates between calibrations.

Figure 3:
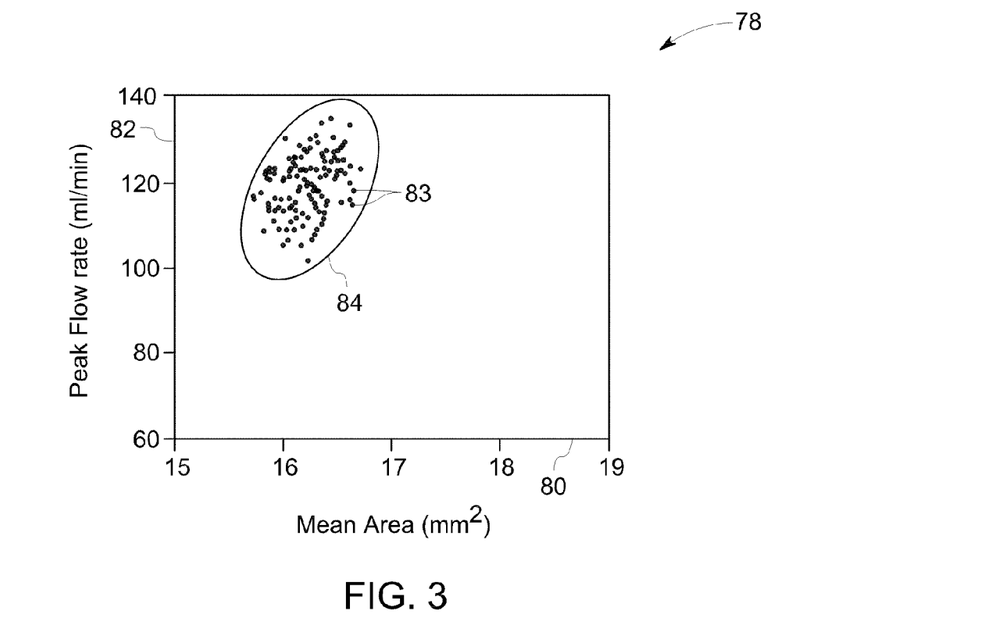
FIG. 3 is an exemplary graphical illustration of a contour in 2D hemodynamic space for mean arterial area and peak blood flow rate identifying the limits on the hemodynamic parameters for the current hemodynamic state.

FIG. 3 is an exemplary illustration 78 of the limits defining the hemodynamic state in a 2D hemodynamic space for arterial area and volumetric flow rate based on a model of the probability distribution. The X-axis 80 represents mean area in $mm^2$, and the Y-axis 82 represents peak flow rate in ml/min. As illustrated herein, the set of points 83 represent multiple measurements used to determine mean and covariance matrix of the hemodynamic parameters. The solid contour 84 around these points represents the limits on the hemodynamic parameters for a given probability threshold. The current hemodynamic state consists of the set of points 83 inside the contour, and a change from the current hemodynamic state consists of any point outside of the contour.

The adaptable arterial compliance model is based on continuous monitoring of the hemodynamic state and multiple previously calibrated compliance curves. The adaptable compliance model uses a current measure of hemodynamic parameters to select among a set of compliance curves calibrated for different hemodynamic states. The multidimensional hemodynamic parameter space is partitioned into decision regions corresponding to these hemodynamic states using pattern classification techniques. The compliance model is selected using the calibrated compliance curve for the closest hemodynamic state to the current hemodynamic parameters. Examples of distance metric include the Euclidean distance in n-dimension space or based on a model of the multivariate probability distribution. When the metric is based on the probability of the distribution, the classifier acts like a maximum likelihood estimator.

Figure 4:
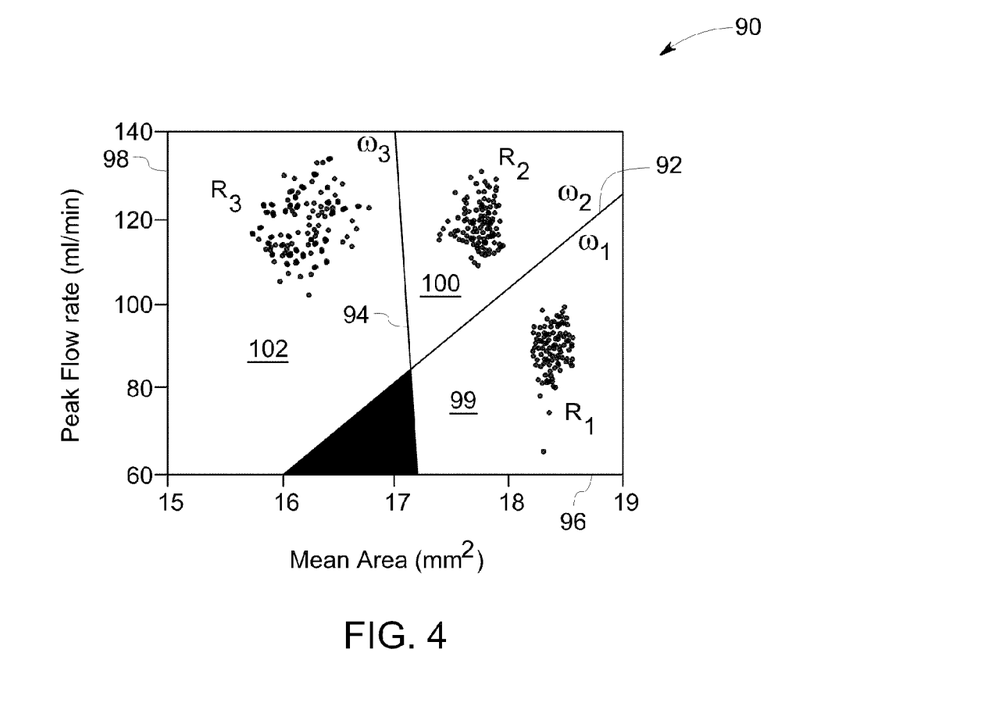
FIG. 4 is a graphical illustration of the partitioning a 2D hemodynamic space for mean arterial area and peak blood flow rate identifying decision boundaries for selecting between several previously calibrated biomechanical model based on the current hemodynamic state.

FIG. 4 is a graphical illustration 90 of partitioning a 2D hemodynamic space for mean arterial area and peak blood flow rate with the straight lines 92, 94 representing the decision boundaries between the different hemodynamic states. The X-axis 96 represents mean area in $mm^2$, and the Y-axis 98 represents peak flow rate in ml/min. In this example, the decision boundaries were formed by bisecting the centroids of the different clusters of points, and the closest previously calibrated hemodynamic state to the current measurements of the hemodynamic parameters is found by $$s = \underset{m=1,\ldots,M}{\operatorname{argmax}} \{d(X|\mu_m)\} \tag{10}$$

where $\mu_m$ and $\Sigma_m$ are the mean vector and covariance matrix for the $m^{th}$ of M calibrated hemodynamic states and X is the current measurement vector. As illustrated herein, the segmentation of area-flow space occurs into three distinct regions 99, 100, 102.

As another example based on the probability for a multivariate normal distribution, the decision for the current hemodynamic state is given $$s = \underset{m=1,\ldots,M}{\operatorname{argmax}} \{P(X \mid \mu_m, \Sigma_m)\} \tag{11}$$

where $\mu_m$ and $\Sigma_m$ are the mean vector and covariance matrix for the $m^{th}$ of M calibrated hemodynamic states and X is the current measurement vector.

An alternative dynamic model to the hard threshold previously described uses a set of weight to perform a weighed average of the multiple calibrated biomechanical models. The weights based on the distance measure have the form $$w_m = \frac{d(X \mid \mu_m)}{\sum_{m=1}^{M} d(X \mid \mu_m)} \tag{12}$$

and the weights based on the probability distribution model has the form $$w_m = \frac{P(X \mid \mu_m, \Sigma_m)}{\sum_{m=1}^{M} P(X \mid \mu_m, \Sigma_m)} \tag{13}$$

The weights are then used to average the parameters of the different biomechanical models or the blood pressure estimates based on the different biomechanical models.

Figure 5:
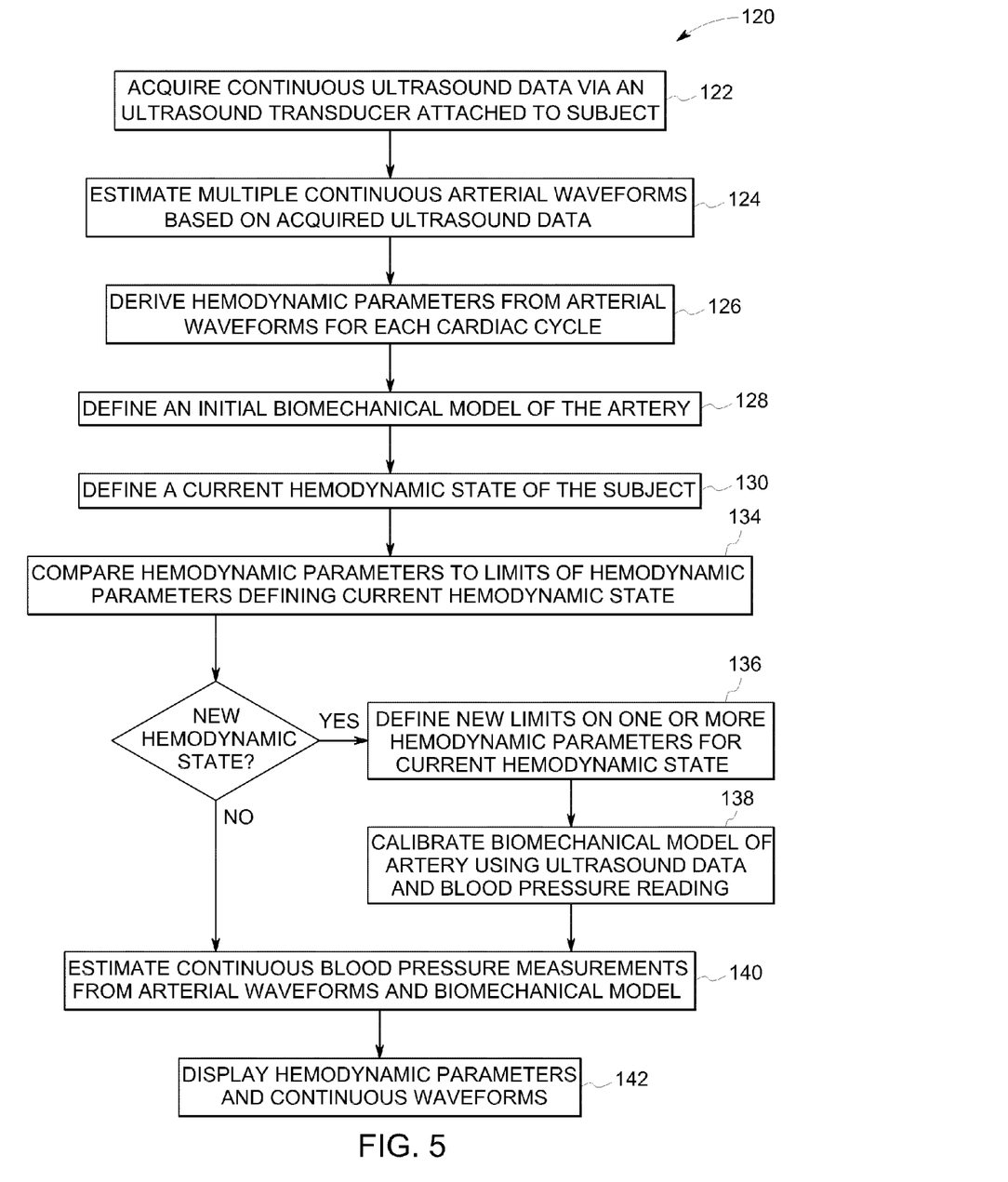
FIG. 5 is a flow chart representing steps in a method for continuous non-invasive hemodynamic state monitoring and continuous blood pressure estimation in a subject in accordance with an embodiment of the invention.

FIG. 5 is a flow chart representing steps in a method 120 for continuous non-invasive hemodynamic state monitoring in a subject. The method 120 includes acquiring continuous ultrasound data via an ultrasound transducer attached to the subject in step 122. In a particular embodiment, ultrasound signals are transmitted into the subject and the reflected ultrasound signals from the subject are received by the ultrasound transducer. The reflected ultrasound signals are converted to electrical signals via the ultrasound transducer and transmitted to a processor. Continuous arterial waveforms are estimated based upon the acquired ultrasound data in step 124. Hemodynamic parameters for each cardiac cycle are derived from the arterial waveforms in step 126. A current hemodynamic state of the subject is defined by setting limits on one or more hemodynamic parameters based upon the variation of the hemodynamic parameters over an initial period of time in step 128. An initial biomechanical model of the artery is defined in step 130 and is calibrated for the current hemodynamic state that converts arterial waveforms into a continuous estimate of arterial blood pressure hemodynamic state of the subject. The hemodynamic state of the subject is continuously monitored based upon the generated hemodynamic parameters from subsequent measurements. The current state of the one or more hemodynamic parameters of the subject is compared in step 134 to previously determined limits for the one or more hemodynamic parameters, wherein the previously determined limits are computed based upon the initial state of one or more hemodynamic parameters. In an event that a change is detected in the current state of the one or more hemodynamic parameters, a trigger signal or alarm is output from a hemodynamic monitor, a current hemodynamic state of the subject is defined in step 136 based on setting new limits for one or more hemodynamic parameters and a biomechanical model is defined for the current hemodynamic state in step 138. In the event that no change is detected, a continuous estimate of the arterial blood pressure is produced using the arterial waveforms and the biomechanical model in step 140. Finally, the hemodynamic parameters, blood pressure estimates, and arterial waveforms are displayed in step 142.

EXAMPLES

The examples that follow are merely illustrative, and should not be construed to be any sort of limitation on the scope of the claimed invention.

An animal experiment was conducted to evaluate the feasibility of the proposed approach for compliance-based blood pressure estimation. A pig was used as a large animal model for the cardiovascular system. The animal was anesthetized and instrumented with an invasive pressure catheter placed in the femoral artery with the location verified using ultrasound. Ultrasound data were acquired with a high frequency vascular ultrasound probe on a cardiovascular ultrasound scanner. The arterial blood pressure was continuously monitored invasively using a pressure sensor mounted on a catheter inserted in the animal's femoral artery. A data acquisition system was used to collect invasive pressure readings at a sample rate of 400 Hz during the entire experiment. Ultrasound B-mode and color flow data were acquired on the femoral artery opposite to the invasive catheter and the ultrasound data was collected at a frame rate of 33 Hz for data segments of approximately 60 seconds in length. The invasive pressure was initially aligned with the ultrasound data using the clocks on the ultrasound and acquisition systems, then more precisely aligned using the peaks in the ultrasound area and invasive pressure waveforms. The invasive pressure was interpolated to the time samples of the ultrasound. In the pig model, cuff-based measurements are difficult to acquire, due to the size of the animal's limbs; therefore periodic cuff reading measurements were simulated from diastolic, mean, and systolic pressures derived from the invasive pressure waveforms.

Figure 6:
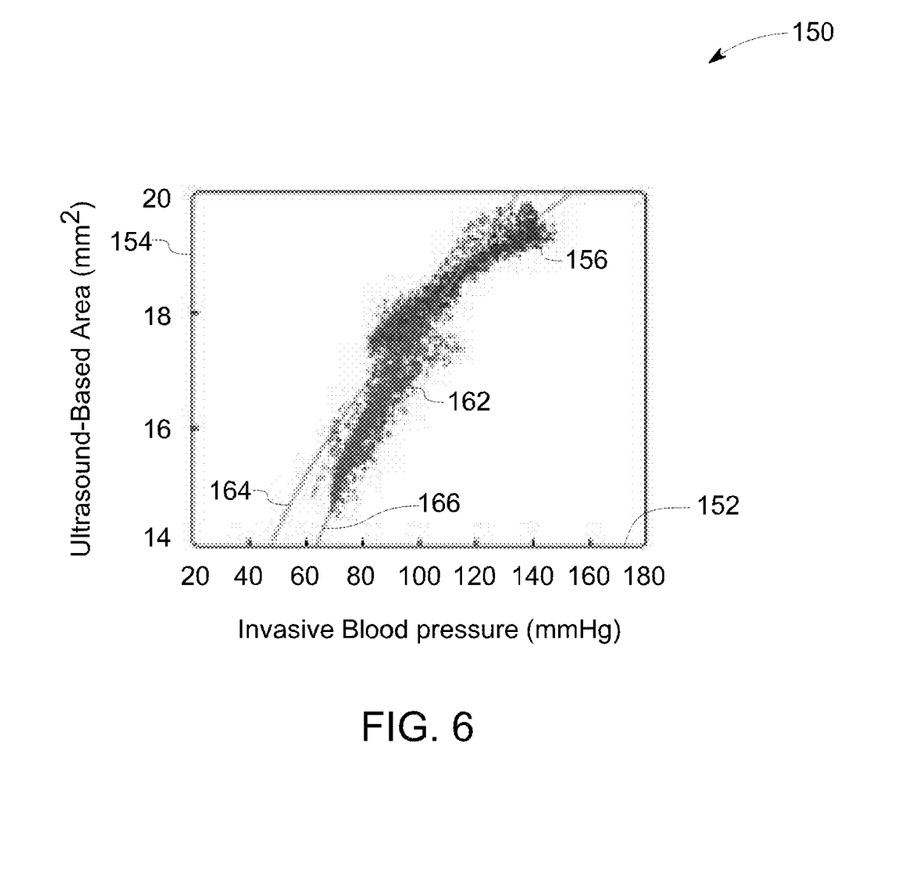
FIG. 6 is an exemplary graphical illustration of scatter plots of the time-aligned invasive pressure and ultrasound area measurements for a data segment prior to injection and a data segment during continuous infusion of sodium nitroprusside in a pig.

Invasive pressure and ultrasound data were collected for a period of time to establish the animal's baseline hemodynamic state. Then sodium nitroprusside, a vaso-dilator, was continuously infused at various rates causing a mean pressure drop of approximately 30 mm Hg. The infusion was stopped and the animal monitored as it returned to the baseline state. FIG. 6 is a graphical illustration of scatter plots 150 of the time-aligned invasive pressure and ultrasound area measurements for a data segment at baseline and a data segment during continuous infusion of sodium nitroprusside. The X-axis 152 represents invasive blood pressure in mmHg and the Y-axis 154 represents ultrasound based area in mm². Scatter plot 156 indicates data segment at a baseline hemodynamic state. Similarly, scatter plot 162 represents data segment during infusion. Additionally, exponential compliance curves 164, 166 were fit respectively to the data for each segment 156, 162 using the diastolic and systolic pressure and area. As illustrated herein, there is a change in both the slope and offset of the compliance curves 164, 166 before and during infusion of the drug with the slope change indicating a higher arterial compliance resulting from the vaso-dilator.

Figure 7:
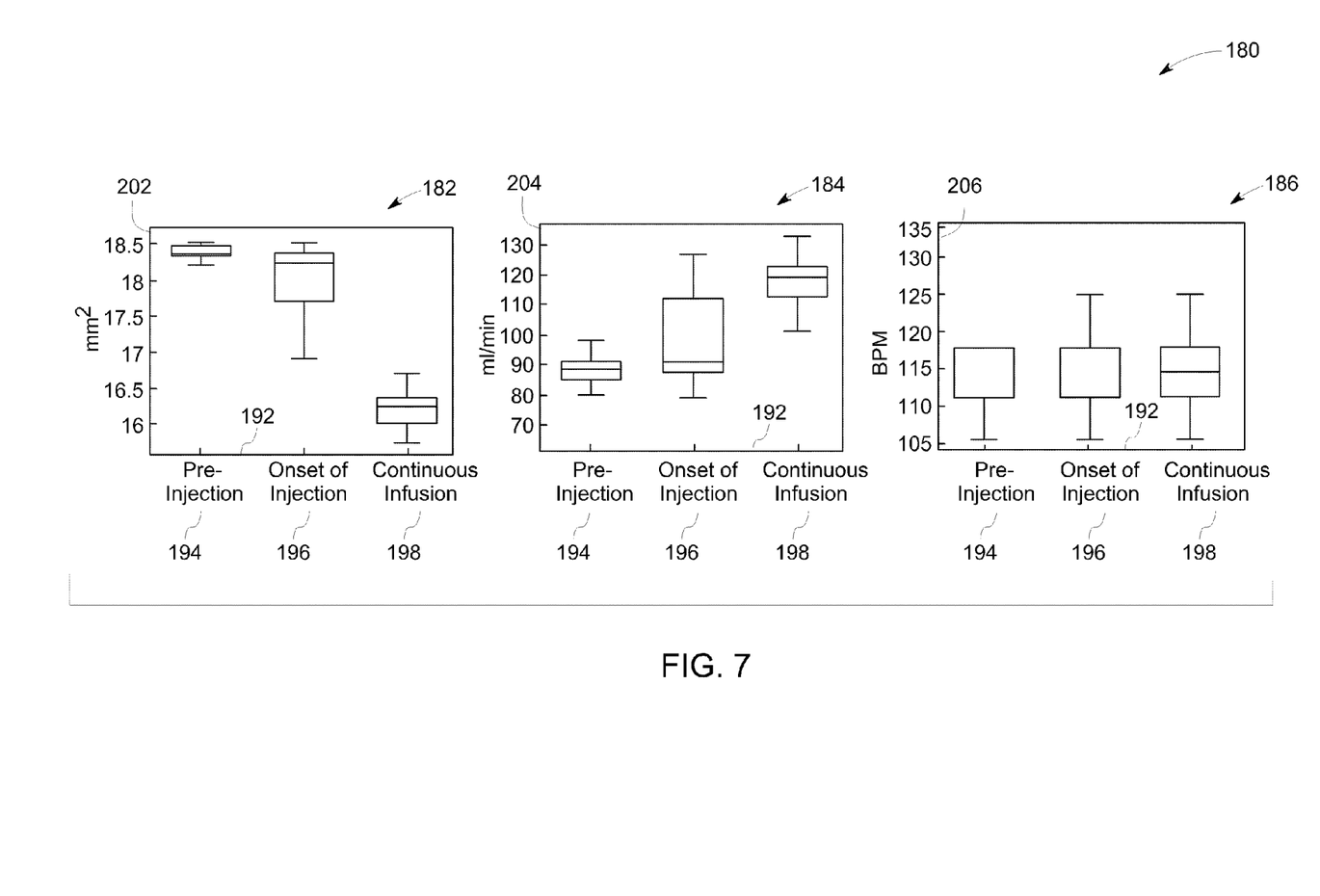
FIG. 7 is an exemplary box and whisker plot showing statistics for the mean arterial area over the cardiac cycle, the peak volumetric flow rate over the cardiac cycle, and the heart rate for three hemodynamic states corresponding to pre-injection, onset of injection and during continuous infusion of sodium nitroprusside.

Furthermore, the ability to detect a change in the hemodynamic state with ultrasound was evaluated. FIG. 7 is a box and whisker plot 180 of an average area over the cardiac cycle, the peak volumetric flow rate over the cardiac cycle, and the heart rate. The average area (182), the peak flow rate (184) and the heart rate (186) were used to define the hemodynamic state for this data set. The X-axes 192 represent three stages specifically, pre-injection referenced by numeral 194, onset of injection 196, and continuous infusion 198. The Y-axis 202 of the average area plot 182 represents area in mm², while the Y-axis 204 of the peak flow rate plot 184 represents flow rate in ml/min. Similarly, the Y-axis 206 of the heart rate plot 186 represents heart rate in beats per minute. As illustrated herein, there was a significant shift 209 in the mean area and peak flow rate with the infusion of the drug at stage 198, while the heart rate was unchanged.

Figure 8:
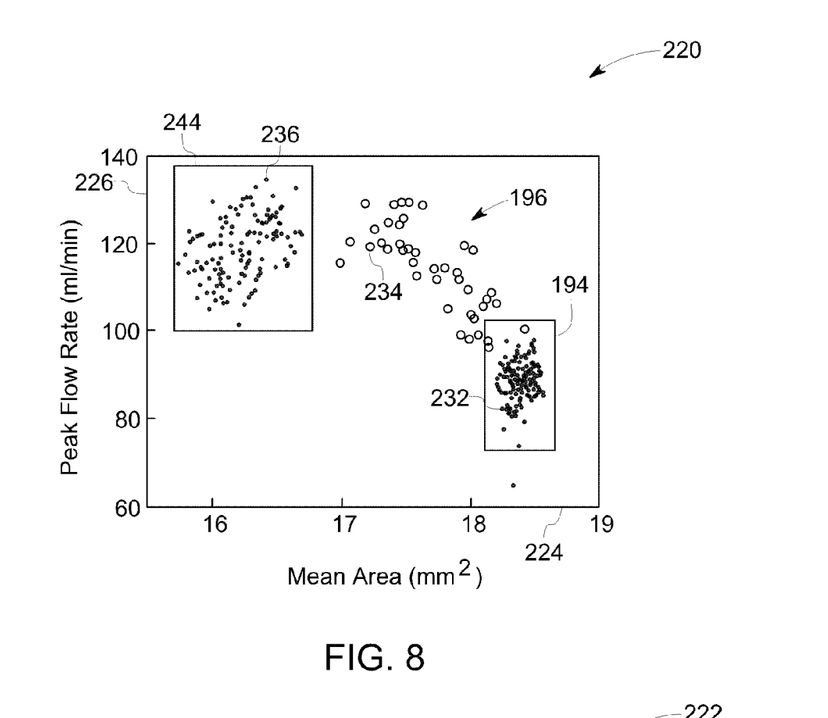
FIG. 8 is an exemplary scatter plot of peak blood flow rate and mean area over a cardiac cycle for three hemodynamic states corresponding to pre-injection, onset of injection and during continuous infusion of sodium nitroprusside.
Figure 9:
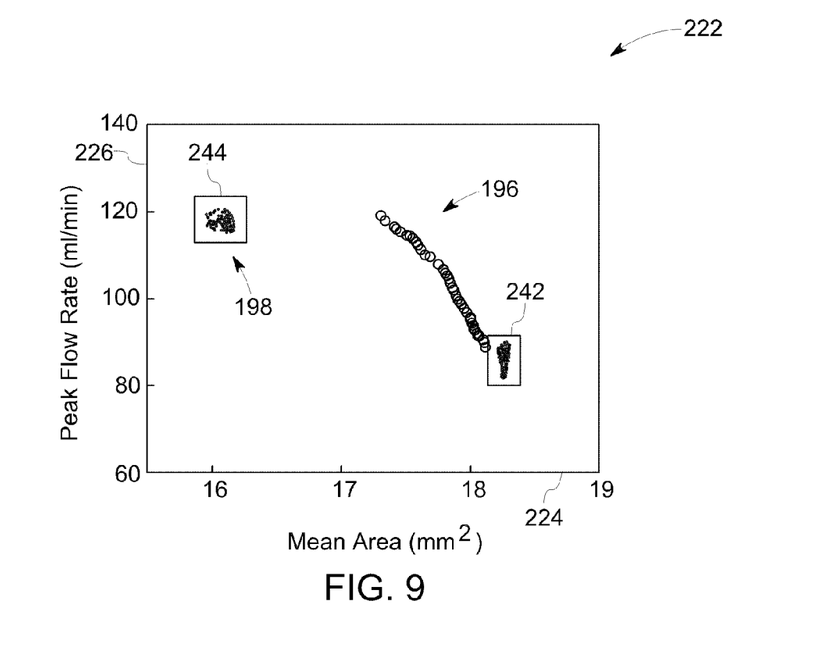
FIG. 9 is an exemplary scatter plot of peak blood flow rate and mean area over averaged over the respiratory cycle for three hemodynamic states corresponding to pre-injection, onset of injection and during continuous infusion of sodium nitroprusside.

The change in the hemodynamic state is better visualized using a 2D scatter plot of the mean area and peak flow, with the heart rate being left out because it was relatively unchanged for this experiment. FIGS. 8 and 9 are scatter plots 220, 222 for the three stages 194, 196 and 198 as referenced in FIG. 7, over a cardiac cycle and over an averaged respiratory cycle respectively. The X-axes 224 represent mean area in mm² and the Y-axes 226 represent peak flow rate in ml/min. Referring to FIG. 8, the baseline points 232, i.e. at pre-injection stage 194, are clustered around one set of values for the area and flow, while the data 234 at the start of the infusion shows there is a transient change in the hemodynamic state before reaching a new steady state 236 during the continuous infusion. Some of the spread in the scatter plots can be attributed to respiration, and a tighter cluster of points is achieved by averaging these parameters over the respiration period, as shown in FIG. 9. Bounding boxes 242, 244 defining the limits on the hemodynamic parameters are also shown in FIGS. 8 and 9 for two hemodynamic states in this experiment corresponding to the baseline state and continuous infusion state.

Figure 10:
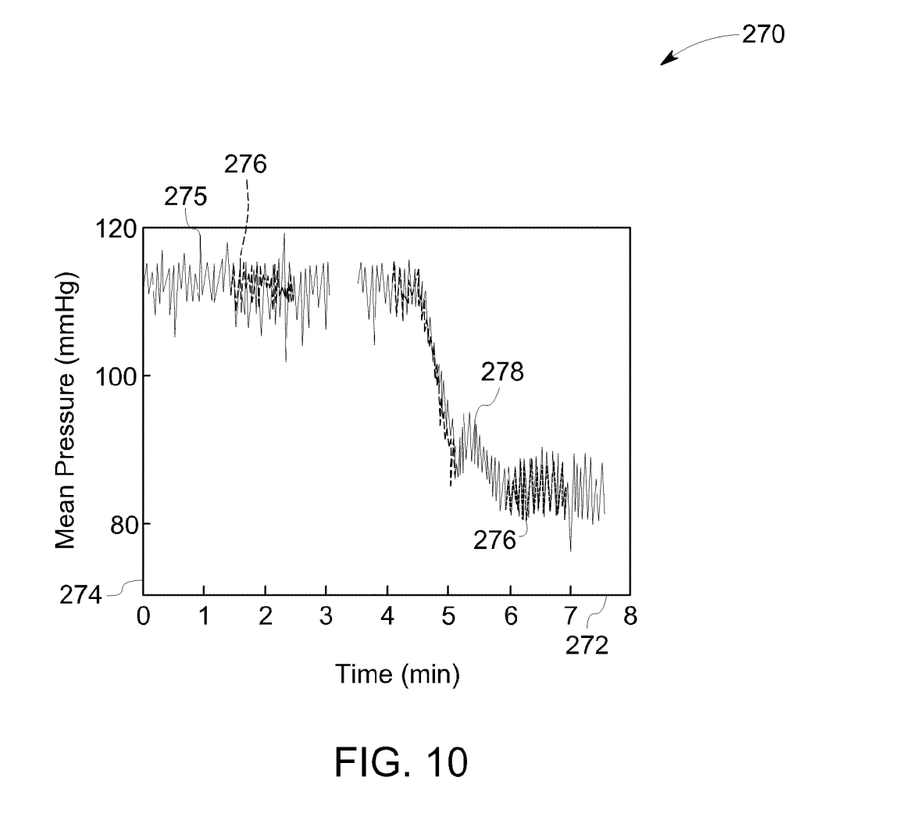
FIG. 10 is an exemplary graphical illustration of continuous, non-invasive blood pressure estimation using the arterial compliance model and ultrasound data acquired before, during and after infusion of sodium nitroprusside.

A final processing step converts the ultrasound measurements into continuous blood pressure measurements. FIG. 10 is a graphical illustration 270 of continuous, non-invasive blood pressure estimation using the compliance model and ultrasound data acquired before, during and after infusion of sodium nitroprusside (vaso-dilator). The X-axis 272 represents time in min, and the Y-axis 274 represents mean arterial pressure in mmHg. The initial calibration of the compliance curve was accomplished using the minimum and maximum of the invasive pressure data (275) and minimum and maximum ultrasound area for a six second window at the start of the baseline data set. This initial compliance curve was used to convert area measurements to blood pressure as shown by curves 276 representing the mean arterial pressure for each cardiac cycle. The periodic variations in the mean pressure waveform correspond to fluctuations in the mean pressure at the respiratory rate. The initial compliance curve was used until a point where the area and flow exceeded the limits defining the bounding box for the baseline state. The compliance model was recalibrated using the minimum and maximum invasive pressure data and the minimum and maximum ultrasound areas in another six second window at the start of the continuous infusion data set and the area converted to blood pressure for the remainder of this data set as shown by the curve 278.

The various embodiments of a system and method for continuous non-invasive monitoring of hemodynamic state described above thus provide a way to achieve a convenient and efficient means of managing rapid changes in the physiological state of a patient. This technique also provides ability to perform measurements with a standard ultrasound scanner and transducer. Further, the system and technique employing automatic detection and processing algorithms eliminate need for an operator to maintain alignment of the probe and perform measurements. Details of automatic detection of vessels using ultrasound may be obtained in patent application US20080119736 A1 entitled "Heart rate demodulation of periodic movement in ultrasound data for object identification" assigned to the same assignee as this application, the entirety of which is hereby incorporated by reference herein.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. For example, the use of a static arterial compliance model described with respect to one embodiment can be adapted for use with an electrocardiograph described with respect to another. Similarly, the various features described, as well as other known equivalents for each feature, can be mixed and matched by one of ordinary skill in this art to construct additional systems and techniques in accordance with principles of this disclosure.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A method for continuous non-invasive hemodynamic state monitoring in a subject comprising:

acquiring continuous ultrasound data via an ultrasound transducer configured to attach to the subject;

estimating a plurality of continuous arterial waveforms based upon the acquired ultrasound data, wherein the continuous arterial waveforms comprise arterial area and volumetric flow rate;

deriving hemodynamic parameters for each cardiac cycle from the arterial waveforms, wherein the hemodynamic parameters comprise at least one of a minimum, a maximum, or an average value of the continuous arterial waveforms over a heart cycle, or a heart rate derived from a period of the arterial waveforms;

defining a current hemodynamic state of the subject by setting limits on one or more hemodynamic parameters based upon the variation of these parameters over an initial period of time, wherein the hemodynamic state is specified by a mean vector and a covariance matrix to remove operator expectation;

defining an initial biomechanical model of the artery using a non-linear compliance curve, as calibrated for the current hemodynamic state that converts arterial waveforms into a continuous estimate of arterial blood pressure, wherein the biomechanical model is a static compliance model extending to a dynamic in vivo situation where acute changes in compliance recalibrate the compliance curve;

continuously monitoring the hemodynamic state of the subject based upon the generated hemodynamic parameters from subsequent measurements;

comparing the current state for one or more hemodynamic parameters of the subject to previously determined limits for one or more hemodynamic parameters, and performing at least one of the following comprising:

outputting a trigger signal or alarm from the hemodynamic state monitor, redefining the current hemodynamic state of the subject by setting new limits for one or more of the hemodynamic parameters based on recent measurements, and calibrating a new biomechanical model for the current hemodynamic state in an event that a change is detected in the current state of one or more hemodynamic parameters; and converting the arterial waveforms into a continuous estimate of the arterial blood pressure using the biomechanical model, and outputting the current hemodynamic parameters, blood pressure estimates, and arterial waveforms in an event that a change in the current state of the one or more hemodynamic parameters is not detected;

wherein the trigger signal or alarm is automatically adjusted based on statistics of the current hemodynamic state.

2. The method of claim 1, wherein the hemodynamic parameters are augmented by one or more hemodynamic parameters comprised of heart rate, respiratory rate and oxygenation level from ancillary monitoring devices attached to the subject.

3. The method of claim 1, wherein the hemodynamic parameters are averaged over the respiratory cycle.

4. The method of claim 1, wherein said subject comprises a living organism.

5. The method of claim 1, further comprising extracting heart rate for each cardiac cycle via an electrocardiograph.

6. The method of claim 1, wherein a change in a state of the one or more hemodynamic parameters comprise a change in values of at least one of diastolic, systolic, and a mean blood pressure.

7. A system for continuous non-invasive hemodynamic state monitoring in a subject comprising:

an ultrasound transducer configured to acoustically couple to the subject configured to acquire a plurality of ultrasound data;

an ultrasound processor coupled to the ultrasound transducer, the ultrasound processor configured to
implement the steps of:
acquiring continuous ultrasound data via the ultrasound transducer; estimating a plurality of continuous arterial waveforms based upon the plurality of ultrasound data, wherein the continuous arterial waveforms comprise arterial area and volumetric flow rate; deriving hemodynamic parameters for each cardiac cycle from the arterial waveforms, wherein the hemodynamic parameters comprise at least one of a minimum, a maximum, or an average value of the continuous arterial waveforms over a heart cycle, or a heart rate derived from a period of the arterial waveforms; defining a current hemodynamic state of the subject by setting limits on one or more hemodynamic parameters based upon the variation of these parameters over an initial period of time, wherein the hemodynamic state is specified by a mean vector and a covariance matrix to remove operator expectation; defining an initial biomechanical model of the artery using a non-linear compliance curve, as calibrated for the current hemodynamic state that converts arterial waveforms into a continuous estimate of arterial blood pressure, wherein the biomechanical model is a static compliance model extending to a dynamic in vivo situation where acute changes in compliance recalibrate the compliance curve; continuously monitoring the hemodynamic state of the subject based upon the generated hemodynamic parameters from subsequent measurements; comparing the current state for one or more hemodynamic parameters of the subject to previously determined limits for one or more hemodynamic parameters, and performing at least one of the following comprising: outputting a trigger signal or alarm from the hemodynamic state monitor, redefining the current hemodynamic state of the subject by setting new limits for one or more of the hemodynamic parameters based on recent measurements, and calibrating a new biomechanical model for the current hemodynamic state in an event that a change is detected in the current state of one or more hemodynamic parameters; and converting the arterial waveforms into a continuous estimate of the arterial blood pressure using the biomechanical model, and outputting the current hemodynamic parameters, blood pressure estimates, and arterial waveforms in an event that a change in the current state of the one or more hemodynamic parameters is not detected; wherein the trigger signal or alarm is automatically adjusted based on statistics of the current hemodynamic state; and a display coupled to the processor configured to output a measured value of the one or more hemodynamic parameters.

* * * * *